United States Patent

[19]

Ooi

[11] Patent Number: 6,014,420
[45] Date of Patent: Jan. 11, 2000

[54] X-RAY CT APPARATUS

[75] Inventor: Junichi Ooi, Muko, Japan

[73] Assignee: Shimadzu Corporation, Kyoto, Japan

[21] Appl. No.: 09/019,741

[22] Filed: Feb. 6, 1998

[30] Foreign Application Priority Data

Feb. 28, 1997 [JP] Japan ................................. 9-045758

[51] Int. Cl.$^7$ ........................................................ A61B 6/03
[52] U.S. Cl. .................................................. 378/19; 378/4
[58] Field of Search ................................... 378/4, 19

[56] References Cited

U.S. PATENT DOCUMENTS

| | | | |
|---|---|---|---|
| 4,559,639 | 12/1985 | Glover et al. | 378/19 |
| 5,131,021 | 7/1992 | Gard et al. | 378/19 |
| 5,469,429 | 11/1995 | Yamazaki et al. | 378/19 |
| 5,579,359 | 11/1996 | Toth | 378/19 |

FOREIGN PATENT DOCUMENTS

| | | |
|---|---|---|
| 0 453 174 | 10/1991 | European Pat. Off. . |
| 0 487 245 | 5/1992 | European Pat. Off. . |

*Primary Examiner*—David Vernon Bruce
*Attorney, Agent, or Firm*—Nikaido, Marmelstein, Murray & Oram, LLP

[57] ABSTRACT

An X-ray CT apparatus is disclosed which has a simple construction and yet is capable of correcting the sensitivity of each X-ray detecting element in response to a focal shift of an X-ray tube. A monitoring detector is formed of eight channels at an end of an X-ray detector for receiving X-rays not penetrating a patient. The eight channels are divided into two regions F and R each having four channels. Each of the regions F and R is divided into two parts along the direction of a body axis. Shielding plates such as of lead (Pb) not penetrable by X rays are applied to the detecting elements in one of the two parts of region F and to those in the other of the two parts of region R. When no focal shift occurs with the X-ray tube, an output difference S0 is zero between a total output F0 of the X-ray detecting elements in the region F and a total output R0 of the X-ray detecting elements in the region R. When a focal shift occurs with the X-ray tube, an output difference S between a total output Rt of the X-ray detecting elements in the region F and a total output Rt of the X-ray detecting elements in the region R corresponds to an amount of shift.

16 Claims, 6 Drawing Sheets

X-RAY CT APPARATUS

BACKGROUND OF THE INVENTION

(1). Field of the Invention

This invention relates to an X-ray CT apparatus including an X-ray source, and an X-ray detector opposed thereto and having an array of numerous X-ray detecting elements, the X-ray source and X-ray detector being revolvable together about an object under examination or a patient to obtain sectional images of the patient.

(2). Description of the Related Art

In an X-ray CT apparatus, a temperature increase in an X-ray tube results in variations in the incidence position of X rays. Then, the sensitivity of X-ray detecting elements varies to give rise to the problem of artifacts appearing in the sectional images obtained. Various causes are conceivable for such variations in the sensitivity of the X-ray detecting elements. In the case of a solid-state detector, such variations may be due to the transmittance or cementing of a scintillator or to an inconstant parallelism of a collimator. In the case of a gas detector of the ionization chamber type, such variations may be caused by each channel having a varying width in the direction of a body axis.

In one conventional technique, therefore, the sensitivity of each detecting element relative to a temperature inside the tube is measured in advance based on scanning conditions and downtime of the tube. A sensitivity level is appropriately selected according to a use situation for actually scanning a patient, in order to correct data obtained from the patient. In another conventional technique, a monitoring detector such as a two-dimensional detector or a line sensor having a resolution in the direction of the patient's body axis is additionally provided to detect a focal shift of the X-ray tube. When the patient is actually scanned, data obtained from the patient are corrected with a predetermined sensitivity correction value according to an X-ray incidence position detected by the monitoring detector.

However, where a correction is made based on a temperature in the tube, actual amounts of focal shift are not detected. Especially, in the event of hysteresis occurring between temperature increase and focal shift of the X-ray tube, it is impossible to make a satisfactory correction of the sensitivity of each X-ray detecting element.

Where a monitoring detector is additionally provided, the apparatus has a complicated overall construction with additional control circuits and so on.

SUMMARY OF THE INVENTION

This invention has been made having regard to the state of the art noted above, and its object is to provide an X-ray CT apparatus having a simple construction and yet capable of correcting the sensitivity of each X-ray detecting element in response to a focal shift of an X-ray tube.

The above object is fulfilled, according to this invention, by an X-ray CT apparatus including an X-ray source, and an X-ray detector opposed thereto and having an array of numerous X-ray detecting elements, the X-ray source and X-ray detector being revolvable together about a patient to obtain sectional images of the patient, the apparatus comprising:

at least two predetermined X-ray detecting elements among the X-ray detecting elements for obtaining output information to provide X-ray incidence position information which is information corresponding to an incidence position of X rays on the X-ray detector;

X-ray shielding masks for covering part of an X-ray incidence plane of the predetermined X-ray detecting elements; and a computing unit for deriving the X-ray incidence position information from the output information obtained from the predetermined X-ray detecting elements, and correcting an influence of a focal shift of the X-ray source by using the X-ray incidence position information to obtain a sectional image of the patient.

In the above apparatus according to this invention, the shielding masks are applied to part of the X-ray incidence plane of the predetermined X-ray detecting elements. When X rays impinges on the X-ray incidence plane, areas of X-ray incidence on the X-ray incidence plane in the regions not covered by the X-ray shielding masks vary with a variation in the incidence position of X rays. The output information obtained from the predetermined X-ray detecting elements varies as a result, and so does the X-ray incidence position information derived from this output information. An X-ray focal shift of the X-ray tube may be detected from the variation of this X-ray incidence position information. It is thus possible to grasp variations in the sensitivity, due to the X-ray focal shift, of X-ray detecting elements receiving X rays having penetrated the patient. The apparatus has a simplified construction since the X-ray detecting elements of the existing X-ray detector are used. Thus, without an increase in manufacturing cost, accurate sectional images of patients may be obtained by correcting the sensitivity of each X-ray detecting element.

In a preferred embodiment of the invention, the predetermined X-ray detecting elements are divided into two groups, a first X-ray shielding mask being applied to one of the groups for covering one side of the X-ray incidence plane of X-ray detecting elements to divide the X-ray incidence plane into two parts along a body axis, a second X-ray shielding mask being applied to the other of the groups for covering one side of the X-ray incidence plane of X-ray detecting elements, opposed to the first shielding mask along the body axis, to divide the X-ray incidence plane into two parts along the body axis.

With the shielding masks applied to the predetermined X-ray detecting elements in this way, different output information is obtained from the X-ray detecting elements of each group. Variations in the incidence position of X rays may be grasped based on the X-ray incidence position information derived from the different output information. An incidence position of X rays on the X-ray detector is grasped more accurately with a simple construction. That is, a focal shift of the X-ray tube may be grasped with increased accuracy.

Preferably, the predetermined X-ray detecting elements are disposed at one end of the X-ray detector for receiving X rays emitted from the X-ray source and reaching the one end directly without penetrating the patient. With this construction, a focal shift of the X-ray tube may be grasped in real time whether a patient is in place or not.

Alternatively, the predetermined X-ray detecting elements may be disposed at opposite ends of the X-ray detector for receiving X rays emitted from the X-ray source and reaching the opposite ends directly without penetrating the patient. If the patient moves right or left, X rays having penetrated the patient may impinge on the predetermined X-ray detecting elements at one end of the X-ray detector. Even so, X rays impinge directly on the predetermined X-ray detecting elements at the other end. Thus, effective X-ray incidence position information may be obtained at all times.

In the apparatus according to this invention, the computing unit may include an X-ray incidence position information deriving device for deriving the X-ray incidence position information from first output information obtained as a result of X rays incident on one group of X-ray detecting elements among the predetermined X-ray detecting elements, and second output information obtained as a result of X ray incident on the other group of X-ray detecting elements, and a correction coefficient deriving device for deriving correction coefficients corresponding to the X-ray incidence position information for each X-ray detecting element forming the X-ray detector. With this construction, the X-ray incidence position information derived by the incidence position information deriving device from the first output information and second output information varies with a difference between the first output information and second output information. The correction coefficient deriving device derives a correction coefficient for each X-ray detecting element of the X-ray detector corresponding to this X-ray incidence position information. That is, the sensitivity of each X-ray detecting element of the X-ray detector may be corrected according to an X-ray focal shift of the X-ray tube.

The incidence position information deriving device may derive a difference between the first output information and the second output information as the X-ray incidence position information. Then, the X-ray incidence position information may be derived from a simple computation.

Preferably, the incidence position information deriving device derives, as the X-ray incidence position information, a difference between the first output information and the second output information, divided by a sum of the first output information and the second output information. With this construction, the X-ray incidence position information may be grasped as a rate of change of the output information from the predetermined X-ray detecting elements. There occurs no influence of a sensitivity reduction due to a degradation of the X-ray detecting elements, for example. That is, the sensitivity of each X-ray detecting element may be corrected with increased accuracy.

In the apparatus according to this invention, the correction coefficient deriving device may derive, as a correction coefficient for each X-ray detecting element, a ratio between reference individual output information which is individual output information obtained for each X-ray detecting element when X rays directly enter the X-ray detector, and individual output information obtained for each X-ray detecting element according to X-ray incidence position information obtained as a result of a focal shift of the X-ray source occurring with further continued entry of X rays to the X-ray detector. With this construction, the correction coefficient deriving device derives a correction coefficient for each X-ray detecting element of the X-ray detector corresponding to the X-ray incidence position information. The sensitivity of each X-ray detecting element may be corrected properly each time the incidence position of X rays varies, to obtain sectional images of a patient with increased accuracy.

The predetermined X-ray detecting elements may comprise a plurality of X-ray detecting elements arranged consecutively, and a shielding mask may be disposed to cover one side of the plurality of X-ray detecting elements to mark a substantially oblique division thereacross, such that an area for shielding a plane of incidence of the X-ray detecting elements gradually varies from one end to the other end of the plurality of X-ray detecting elements. With this construction, an area of X-ray incidence in the region not covered by the X-ray shielding mask varies with a variation in the incidence position of X rays. The X-ray incidence position information based on the output information obtained from the predetermined X-ray detecting elements varies as a result. Thus, an X-ray focal shift may be detected with a simplified construction.

Preferably, the predetermined X-ray detecting elements are disposed at one end of the X-ray detector for receiving X rays emitted from the X-ray source and reaching the one end directly without penetrating the patient. With this construction, a focal shift of the X-ray tube may be grasped in real time whether a patient is in place or not.

Alternatively, for example, the predetermined X-ray detecting elements may be disposed at opposite ends of the X-ray detector for receiving X rays emitted from the X-ray source and reaching the opposite ends directly without penetrating the patient.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Embodiments of this invention will be described hereinafter with reference to FIGS. 1 through 7.

Figure 1:
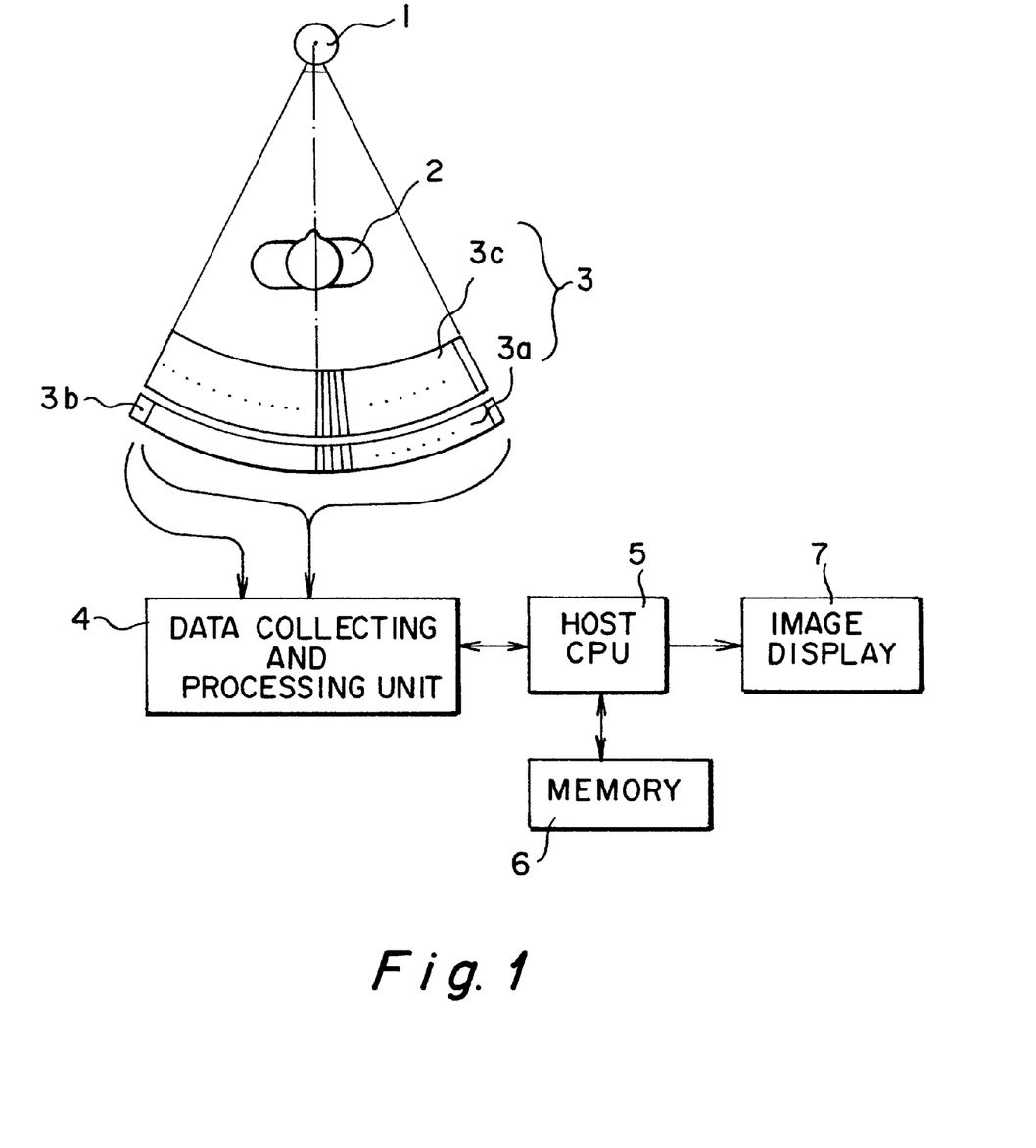
FIG. 1 is a schematic view of an X-ray CT apparatus according to this invention.

FIG. 1 is a schematic view of an X-ray CT apparatus embodying the invention. The apparatus includes an X-ray tube 1 and an X-ray detecting unit 3 opposed to each other across a patient 2. The X-ray tube 1 and X-ray detecting unit 3 are revolvable together while irradiating the patient 2 with X rays from the X-ray tube 1, whereby the X-ray detecting unit 3 provides X-ray penetration data of the patient 2 taken from an approximately 180° direction and an approximately 360° direction.

The X-ray detecting unit 3 includes a collimator 3c for collimating incident X rays, and an X-ray detector having an imaging X-ray detector 3a and a monitoring detector 3b for detecting the X rays. The X-ray detector includes X-ray detecting elements arranged arcuately about the X-ray tube 1 to define approximately 500 to 1,000 channels. The detecting elements are formed of scintillator elements for converting X rays into light, and photodiodes for detecting the light converted by the scintillator elements and outputting it as electric signals.

The imaging X-ray detector 3a is used to pick up images of the patient 2. The monitoring detector 3b is used to detect a focal shift of the X-ray tube 1. For this purpose, the monitoring detector 3b is formed of predetermined X-ray detecting elements arranged in a position for receiving X rays not penetrating the patient 2.

A data collecting and processing unit 4 collects data from the respective channels, performs necessary processes such as amplification, and digitizes the data for output to a host CPU 5.

The host CPU 5, besides controlling operation of the entire apparatus, corrects the sensitivity of each X-ray detecting element in response to a focal shift of the X-ray tube 1, based on correction coefficients stored in a memory 6, carries out computations necessary for image reconstruction, and then causes an image display 7 to display sectional images obtained. The processes performed by the host CPU 5 correspond to the functions of the computing unit in this invention.

Figure 2:
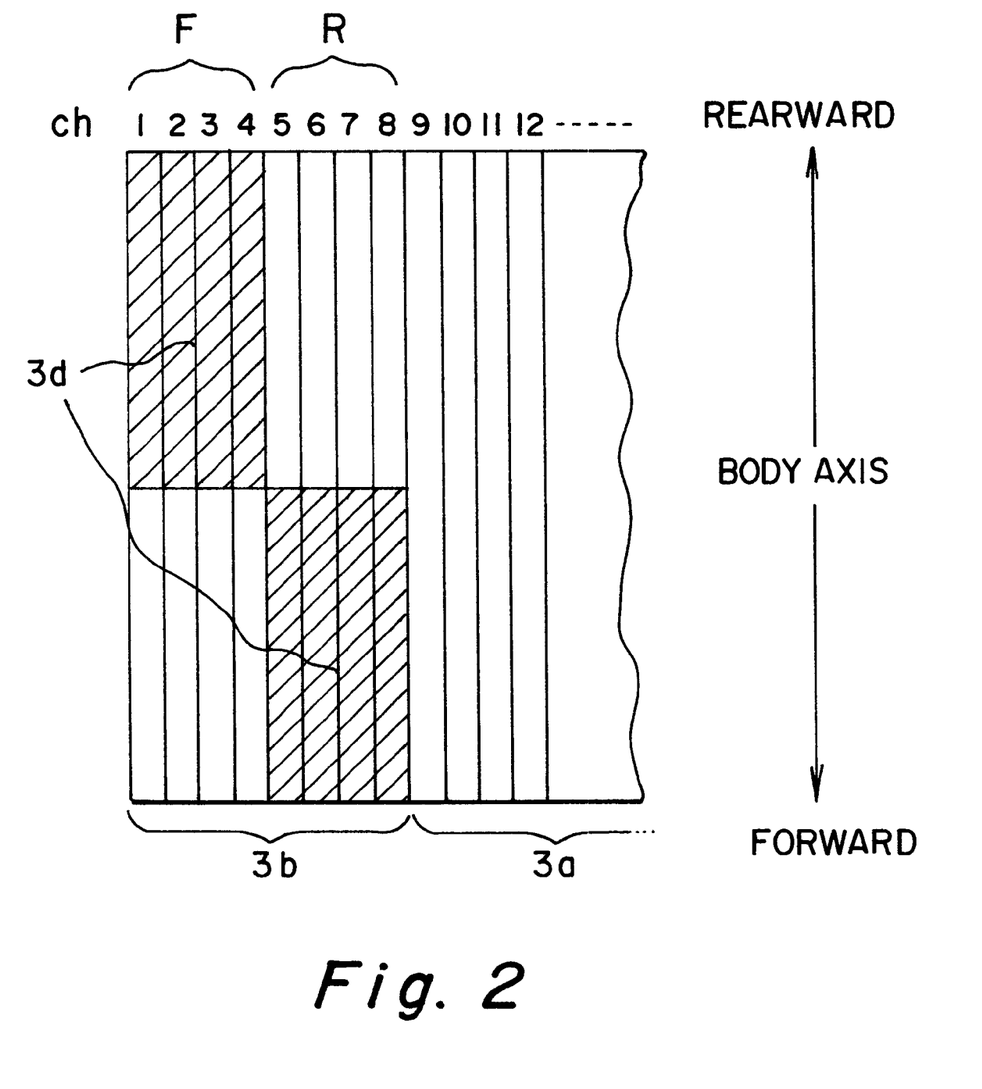
FIG. 2 is a view showing an X-ray detector and X-ray shielding masks according to this invention.

FIG. 2 shows part of the imaging X-ray detector 3a and the monitoring detector 3b seen from a plane of X-ray incidence. The monitoring detector 3b is formed of eight channels at an end of the X-ray detector for receiving X-rays not penetrating the patient 2. The eight channels are divided into two regions F and R each having four channels. Each of the regions F and R is divided into two parts along the direction of a body axis. Shielding plates 3d such as of lead (Pb) not penetrable by X rays are applied to the detecting elements in one of the two parts of region F (i.e. the rearward part in FIG. 2) and to those in the other of the two parts of region R (i.e. the forward part in FIG. 2). The shielding plates 3d arranged in the respective regions F and R correspond to the first shielding mask and second shielding mask in this invention.

Figure 3A:
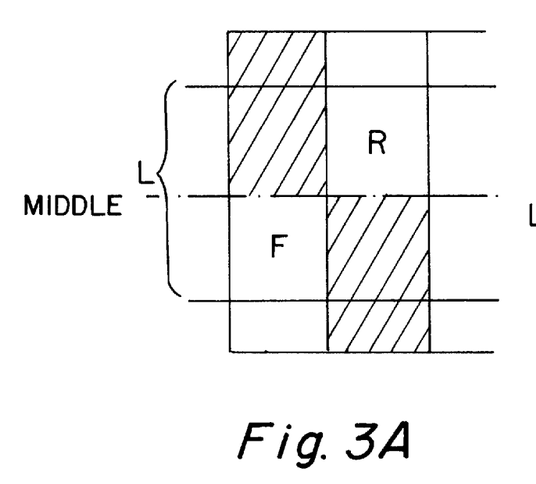
FIGS. 3A and 3B are explanatory views of X rays moving on the X ray detector with a focal shift of the X-ray tube.
Figure 3B:
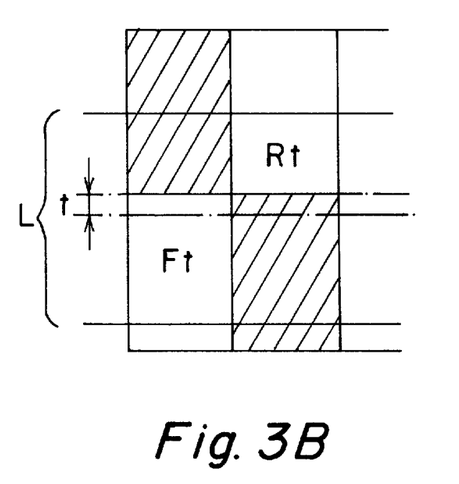
Figure 4:
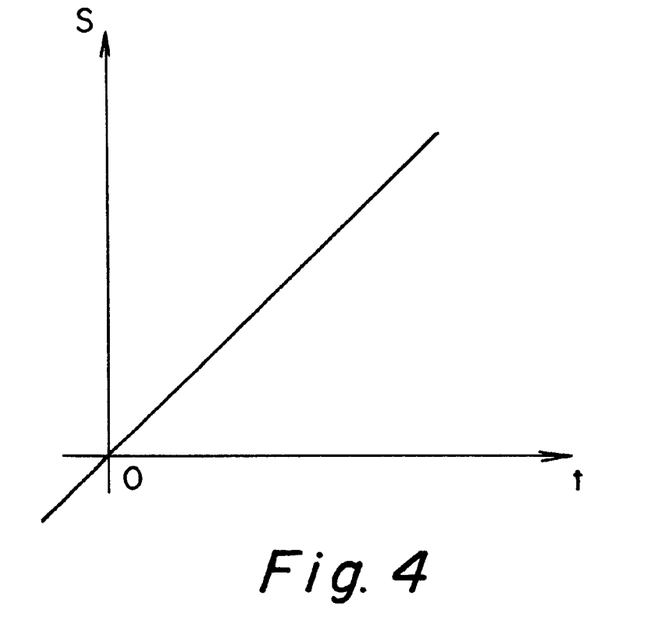
FIG. 4 is a view showing a relationship between focal shift and focal shift corresponding value.

As shown in FIG. 3A, when no focal shift occurs with the X-ray tube 1, that is when a bundle of X rays L enters a middle portion of the X-ray detector, an output difference S0 is zero between a total output F0 of the X-ray detecting elements in the region F and a total output R0 of the X-ray detecting elements in the region R. As shown in FIG. 3B, when a focal shift occurs with the X-ray tube 1, e.g. when a bundle of X rays L is shifted by an amount t forwardly along the body axis, an output difference S between a total output Ft of the X-ray detecting elements in the region F and a total output Rt of the X-ray detecting elements in the region R corresponds to the amount of shift t. It is thus possible to obtain a value corresponding to the X-ray focal shift (hereinafter called "focal shift corresponding value") from the outputs of the X-ray detecting elements of the monitoring detector 3b. Usually, the X-ray focal shift t (which is regarded as a shift of X-ray bundle L for simplicity) and the above output difference S (which is hereinafter simulated by "focal shift corresponding value") are in a substantially linear relationship as shown in the graph of FIG. 4.

The total output Ft and total output Rt correspond to the first output information and second output information of this invention, respectively. The focal shift corresponding value obtained from the outputs of the X-ray detecting elements of the monitoring detector 3b and corresponding to the X-ray focal shift corresponds to the X-ray incidence position information of this invention.

Where the X-ray detector is a solid-state detector, its sensitivity lowers due to a degradation of radiation as a result of continued X-ray incidence. Such influence is eliminated by a correction with the sensitivity over an entire incidence range of X rays L, more particularly by using a focal shift corresponding value St derived from the following equation:

$$St=(Ft-Rt)/(Ft+Rt)$$

The above equation normalizes the output difference representing the amount of shift with data of the entire incidence range of X rays L. Thus, such a correction also corrects influences of sensitivity variations of the detector due to temperature variations.

For the focal shift corresponding value St, (Ft−Rt) or (Ft−Rt)/(Ft+Rt) may be selected appropriately according to the X-ray detector used. Any value may be adopted as long as it corresponds uniquely to a focal shift of the X-ray tube 1.

The process of computing the focal shift corresponding value St corresponds to the function of the incidence position information deriving device of this invention.

A correction coefficient Tik for correcting the focal shift is derived from the following equation:

$$Tik=Ai0/Aik \; (i=1 \text{ to } n)$$

where Ai0 is ith (ith X-ray detecting element) output value of the imaging X-ray detector 3a in the event of no focal shift, Aik is ith output value of the image X-ray detector 3a when the focal shift corresponding value is Sk, and n is a total number of channels in the imaging X-ray detector 3a.

Figure 5:
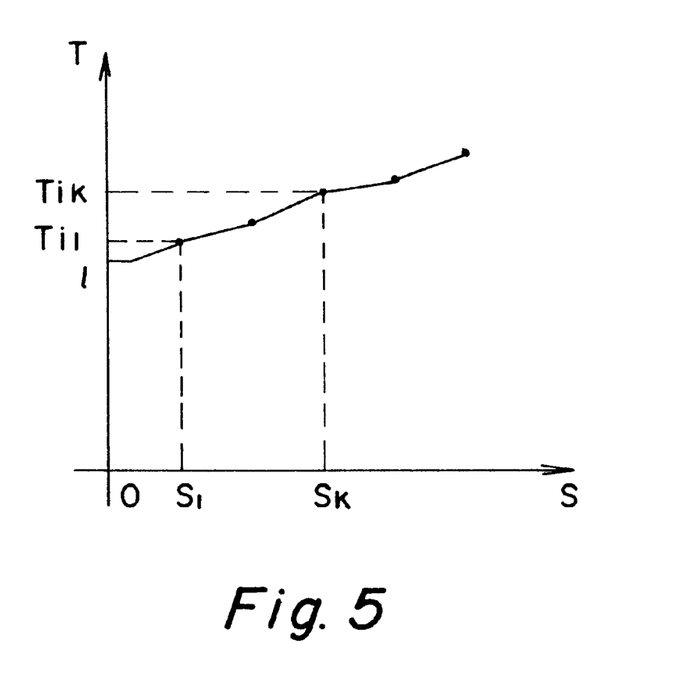
FIG. 5 is a view showing a relationship between focal shift corresponding value and correction coefficient.

The host CPU 5 causes a continuous incidence of X rays in the absence of patient 2, computes focal shift corresponding values Sk obtained from outputs of the X-ray detecting elements of the monitoring detector 3b through the data collecting and processing unit 4, successively computes correction coefficients Tik for the focal shift corresponding values Sk, determines a relationship as shown in FIG. 5 for each channel i, and stores such relationships in the memory 6. These operations are performed before an actual image pickup from the patient 2.

The focal shift corresponding values are obtained as consecutive values. Since correction coefficients Tik are stored in the memory 6, only predetermined discrete values Sk (k=0 to m (Sm being a maximum focal shift corresponding value which may occur in time of an actual image pickup)) are stored.

Figure 6:
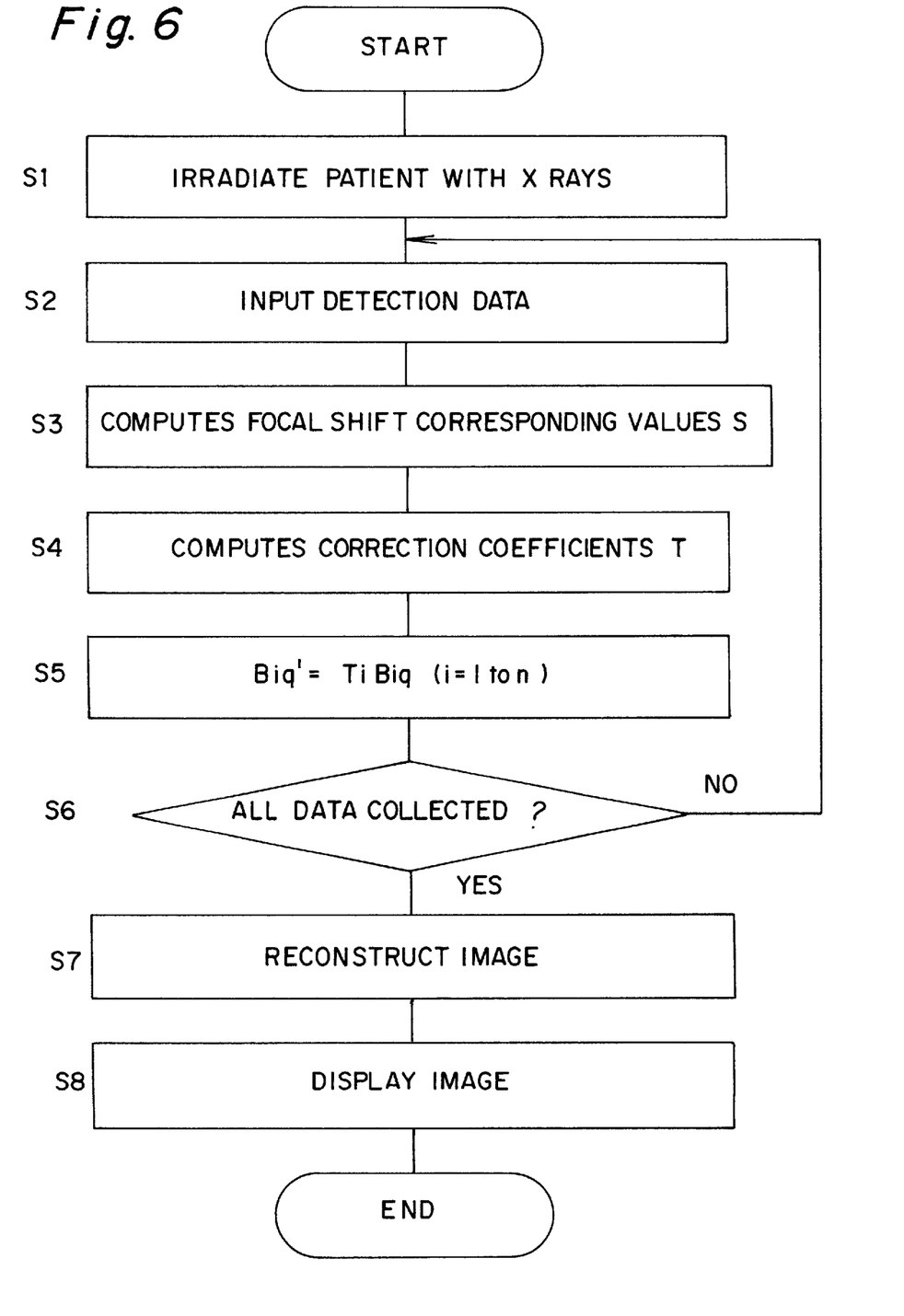
FIG. 6 is a flowchart of an operation of this invention.

Next, an operation of this invention for picking up images of the patient 2 will be described with reference to the flowchart of FIG. 6 showing operations of the host CPU 5. An X-ray image pickup is performed for the patient 2 after necessary correction coefficients Tik are stored in the memory 6.

First, the patient 2 is placed between the X-ray tube 1 and X-ray detecting unit 3 and irradiated with X rays while the X-ray tube 1 and X-ray detecting unit 3 are revolved together about the patient 2 (S1).

Next, the host CPU 5 (S2) receives detection data from the imaging X-ray detector 3a and monitoring detector 3b through the data collecting and processing unit 4 which successively outputs the data. The host CPU 5 computes focal shift corresponding values S based on the detection data obtained from the monitoring detector 3b (S3).

When the focal shift corresponding values S have been obtained, the host CPU 5 computes a correction coefficient Ti for each channel i from a table of correspondence between focal shift corresponding value S and correction coefficient T as shown in FIG. 5 and stored beforehand in the memory 6 for the respective channels of the imaging X-ray detector 3a (S4).

The process of computing the correction coefficients Ti performed at step S4 corresponds to the function of the correction coefficient deriving device of this invention.

The correction coefficients are stored discretely in relation to the focal shift corresponding values Sk. Therefore, when the focal shift corresponding values S obtained are between Sp and Sp+1 for example, the correction coefficients Ti actually used may be derived from the following equation:

T$i$=(T$ip$+1−T$ip$)·(S−S$p$)/(S$p$+1−S$p$)

When the correction coefficients Ti have been obtained, all detection data Biq(i=1 to n) obtained from the imaging X-ray detector 3$a$ in time of image pickup are corrected based on the following equation (S5):

B$iq'$=T$i$·B$iq$ ($i$=1 to $n$)

where i is a channel number of the image X-ray detector 3$a$, and q is a data collection number. Usually, 1000 to 2000 data are collected for one image picked up.

The above operation is carried out until all the data are collected (S6). When all the data have been collected, an image reconstruction processing is carried out based on the corrected detection data of image X-ray detector 3$a$ to obtain a sectional image (S7).

The sectional image obtained is displayed on the image display 7 (S8).

Figure 7:
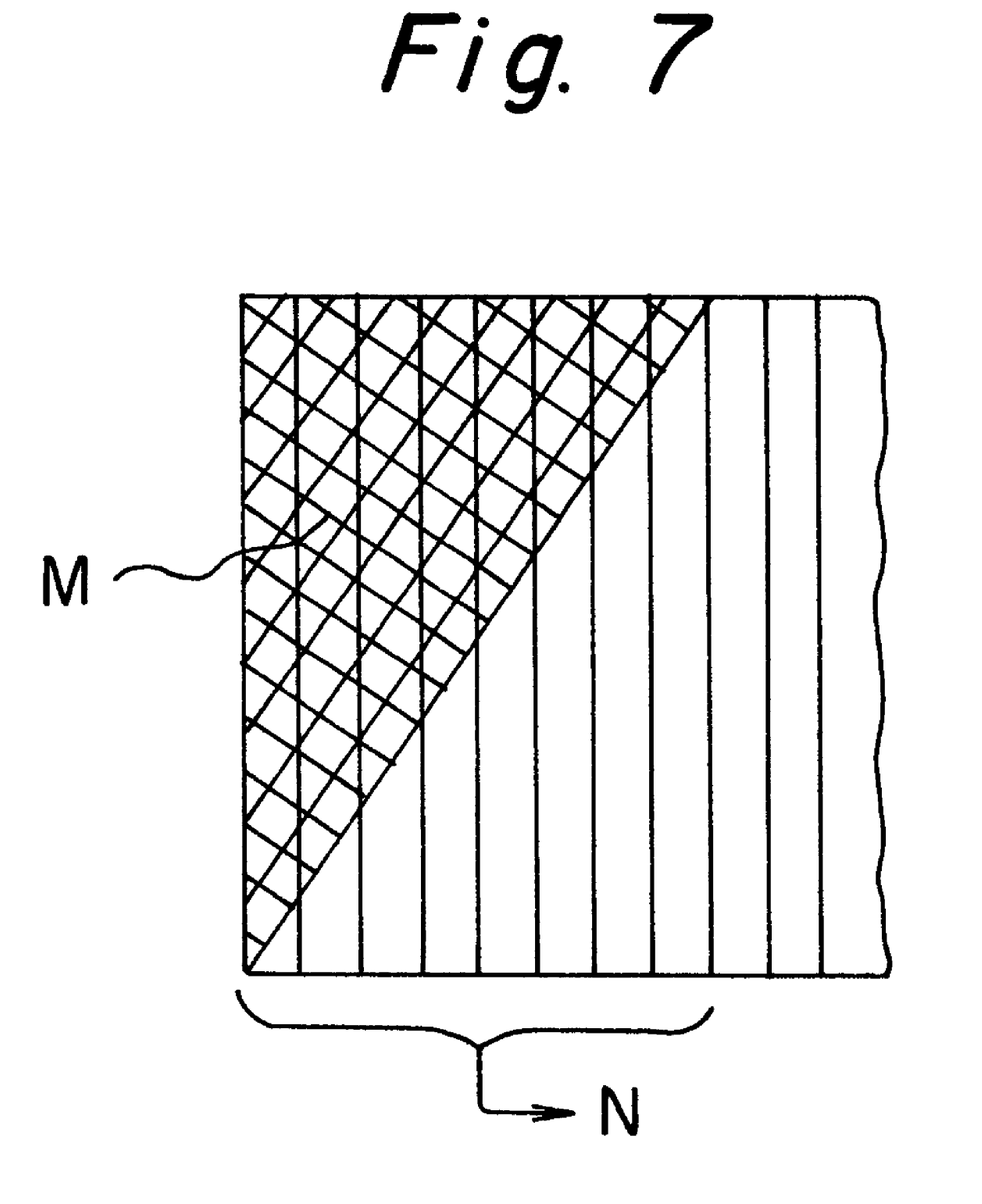
FIG. 7 is a view showing a modified X-ray shielding mask according to this invention.

FIG. 7 shows a shielding mask in another embodiment of this invention. A shielding plate M such as of lead (Pb) not penetrable by X rays is applied to predetermined X-ray detecting elements at an end of an X-ray detector for receiving X-rays not penetrating the patient 2. The shielding plate M covers these detecting elements with an edge thereof of the shielding plate M extending obliquely. In this embodiment, as in the embodiment shown in FIG. 2, focal shift corresponding values uniquely corresponding to a focal shift are obtained.

In the above embodiments, the monitoring detector 3$b$ including the predetermined X-ray detecting elements is disposed at an end of the X-ray detecting unit 3. This invention is not limited to such construction. For example, monitoring detectors 3$b$ may be arranged at opposite ends of the X-ray detecting unit 3.

In the above embodiments, the eight predetermined X-ray detecting elements are divided into two groups each having four detecting elements. This invention is not limited thereto. For example, two X-ray detecting elements may be divided into one each. Thus, the number of predetermined X-ray detecting elements according to this invention may be any number, only if it is two or more.

Further, while, in the above embodiments, the predetermined X-ray detecting elements are divided into two groups, they may be divided into three or more groups, for example. Then, X-ray incidence position information may be derived from output information provided by the X-ray detecting elements in the respective groups.

The present invention may be embodied in other specific forms without departing from the spirit or essential attributes thereof and, accordingly, reference should be made to the appended claims, rather than to the foregoing specification, as indicating the scope of the invention.

What is claimed is:

1. An X-ray CT apparatus including an X-ray source, and an X-ray detector opposed thereto to receive X-rays from a first direction and having an array of numerous X-ray detecting elements positioned adjacent to each other in a second direction, the second direction being perpendicular to the first direction, the X-ray source and X-ray detector being revolvable together about a patient to obtain sectional images of the patient, said apparatus comprising:

at least two predetermined X-ray detecting elements among said X-ray detecting elements for obtaining output information to provide X-ray incidence position information which is information corresponding to an incidence position of the X-rays on said X-ray detector, said at least two predetermined X-ray elements including first and second X-ray detecting elements each having an X-ray incidence plane with a top portion and a bottom portion arranged in a third direction, the third direction being substantially perpendicular to the first and second directions;

a first X-ray shielding mask masking the bottom portion of the first X-ray detecting element;

a second X-ray shielding mask masking a top portion of the second X-ray detecting element; and computing means for deriving said X-ray incidence position information from said output information obtained from said predetermined X-ray detecting elements, and correcting an influence of a focal shift of said X-ray source by using said X-ray incidence position information to obtain a sectional image of said patient.

2. An X-ray CT apparatus as defined in claim 1, wherein said predetermined X-ray detecting elements are divided into two groups, each group including a plurality of X-ray detecting elements, the first X-ray shielding mask being applied to one of said groups masking bottom portions of said one of said groups of X-ray detecting elements, the second X-ray shielding mask being applied to the other of said groups masking top portions of said other of said groups of X-ray detecting elements.

3. An X-ray CT apparatus as defined in claim 1, wherein said predetermined X-ray detecting elements are disposed at one end of said X-ray detector for receiving X rays emitted from said X-ray source and reaching said one end directly without penetrating said patient.

4. An X-ray CT apparatus as defined in claim 1, wherein said predetermined X-ray detecting elements are disposed at opposite ends of said X-ray detector for receiving X rays emitted from said X-ray source and reaching said opposite ends directly without penetrating said patient.

5. An X-ray CT apparatus as defined in claim 1, wherein the X-ray incidence planes of the first and second X-ray detecting elements only include the top and bottom portions, and wherein the top portions of the first and second X-ray detecting elements are equal in size and wherein the bottom portions of the first and second X-ray detecting elements are equal in size.

6. An X-ray CT apparatus as defined in claim 1, wherein the first X-ray shielding mask is separate from the second X-ray shielding mask.

7. An X-ray CT apparatus as defined in claim 1, wherein the first and second X-ray shielding masks are rectangular.

8. An X-ray CT apparatus as defined in claim 1, wherein said computing means includes X-ray incidence position information deriving means for deriving said X-ray incidence position information from first output information obtained as a result of X-rays incident on the first X-ray detecting element, and second output information obtained as a result of X-rays incident on the second X-ray detecting element, and correction coefficient deriving means for deriving correction coefficients corresponding to said X-ray incidence position information for each X-ray detecting element forming said X-ray detector.

9. An X-ray CT apparatus as defined in claim 8, wherein said incidence position information deriving means derives a difference between said first output information and said second output information as said X-ray incidence position information.

10. An X-ray CT apparatus as defined in claim 8, wherein said incidence position information deriving means derives, as said X-ray incidence position information, a difference between said first output information and said second output information, divided by a sum of said first output information and said second output information.

11. An X-ray CT apparatus as defined in claim 8, wherein said correction coefficient deriving means derives, as a correction coefficient for each X-ray detecting element, a ratio between reference individual output information which is individual output information obtained for each X-ray detecting element when X rays directly enter said X-ray detector, and individual output information obtained for each X-ray detecting element according to X-ray incidence position information obtained as a result of a focal shift of said X-ray source occurring with further continued entry of X rays to said X-ray detector.

12. An X-ray CT apparatus including an X-ray source, and an X-ray detector opposed thereto and having an array of numerous X-ray detecting elements, the X-ray source and X-ray detector being revolvable together about a patient to obtain sectional images of the patient, said apparatus comprising:

at least two predetermined X-ray detecting elements among said X-ray detecting elements for obtaining output information to provide X-ray incidence position information which is information corresponding to an incidence position of the X-rays on said X-ray detector;

X-ray shielding masks for covering part of an X-ray incidence plane of said predetermined X-ray detecting elements; and computing means for deriving said X-ray incidence position information from said output information obtained from said predetermined X-ray detecting elements, and correcting an influence of a focal shift of said X-ray source by using said X-ray incidence position information to obtain a sectional image of said patient; and wherein said computing means includes X-ray incidence position information deriving means for deriving said X-ray incidence position information from first output information obtained as a result of X-rays incident on one group of X-ray detecting elements among said predetermined X-ray detecting elements, and second output information obtained as a result of X-rays incident on the other group of X-ray detecting elements, and correction coefficient deriving means for deriving correction coefficients corresponding to said X-ray incidence position information for each X-ray detecting element forming said X-ray detector;

wherein said correction coefficient deriving means derives, as a correction coefficient for each X-ray detecting element, a ratio between reference individual output information which is individual output information obtained for each X-ray detecting element when X-rays directly enter said X-ray detector, and individual output information obtained for each X-ray detecting element according to X-ray incidence position information obtained as a result of a focal shift of said X-ray source occurring with further continued entry of X rays to said X-ray detector.

13. An X-ray CT apparatus as defined in claim 12, wherein said predetermined X-ray detecting elements are disposed at one end of said X-ray detector for receiving X-rays emitted from said X-ray source and reaching said one end directly without penetrating said patient.

14. An X-ray CT apparatus as defined in claim 12, wherein said predetermined X-ray detecting elements are disposed at opposite ends of said X-ray detector for receiving X-rays emitted from said X-ray source and reaching said opposite ends directly without penetrating said patient.

15. An X-ray CT apparatus as defined in claim 12, wherein said incidence position information deriving means derives a difference between said first output information and said second output information as said X-ray incidence position information.

16. An X-ray CT apparatus as defined in clam 8, wherein said incidence position information deriving means derives, as said X-ray incidence position information, a difference between said first output information and said second output information, divided by a sum of said first output information and said second output information.

* * * * *